US00PP20551P3

(12) United States Plant Patent
Lane

(10) Patent No.: US PP20,551 P3
(45) Date of Patent: Dec. 15, 2009

(54) CHERRY TREE NAMED '13S2009'

(50) Latin Name: *Prunus avium*
Varietal Denomination: 13S2009

(75) Inventor: W. David Lane, Summerland (CA)

(73) Assignee: Her Majesty the Queen in right of Canada, as represented by the Minister of Agriculture and Agri-Food Canada, Summerland (CA)

( * ) Notice: Subject to any disclaimer, the term of this patent is extended or adjusted under 35 U.S.C. 154(b) by 763 days.

(21) Appl. No.: 10/379,714

(22) Filed: Mar. 6, 2003

(65) Prior Publication Data

US 2004/0045061 P1 Mar. 4, 2004

Related U.S. Application Data

(60) Provisional application No. 60/363,547, filed on Mar. 13, 2002.

(51) Int. Cl.
*A01H 5/00* (2006.01)

(52) U.S. Cl. ..... Plt./181

(58) Field of Classification Search ..... Plt./181
See application file for complete search history.

(56) References Cited

PUBLICATIONS

UPOV hit '13S2009', UPOV–rom Plant Variety Database, Mar. 2003.*
Manual of Patent Examining Procedure (MPEP) pp. 700/234 to 700/243. USPTO Aug. 2006.*

* cited by examiner

*Primary Examiner*—Annette H Para
(74) *Attorney, Agent, or Firm*—Penny J. Aguirre

(57) ABSTRACT

A new and distinct variety of cherry tree named '13S2009' with the following characteristics. '13S2009' has large flattened-heart shaped fruit, with shiny, dark red skin and red to dark red flesh. The fruit has a non-prominent suture and a flat to slightly hollow apex. The fruit matures very late in the harvest season, about 27 days after 'Van' and 'Bing' and 8 days after 'Sweetheart'. The flesh of the fruit is very firm, and has a moderately sweet taste. The fruit are tolerant to rain splitting. The stone of '13S20-09' is intermediate in lateral view, large in size, and has strongly developed keel. The tree is upright to spreading, self-compatible, moderately vigorous and has produced good, crops annually since fruiting commenced.

3 Drawing Sheets

Figure 1:
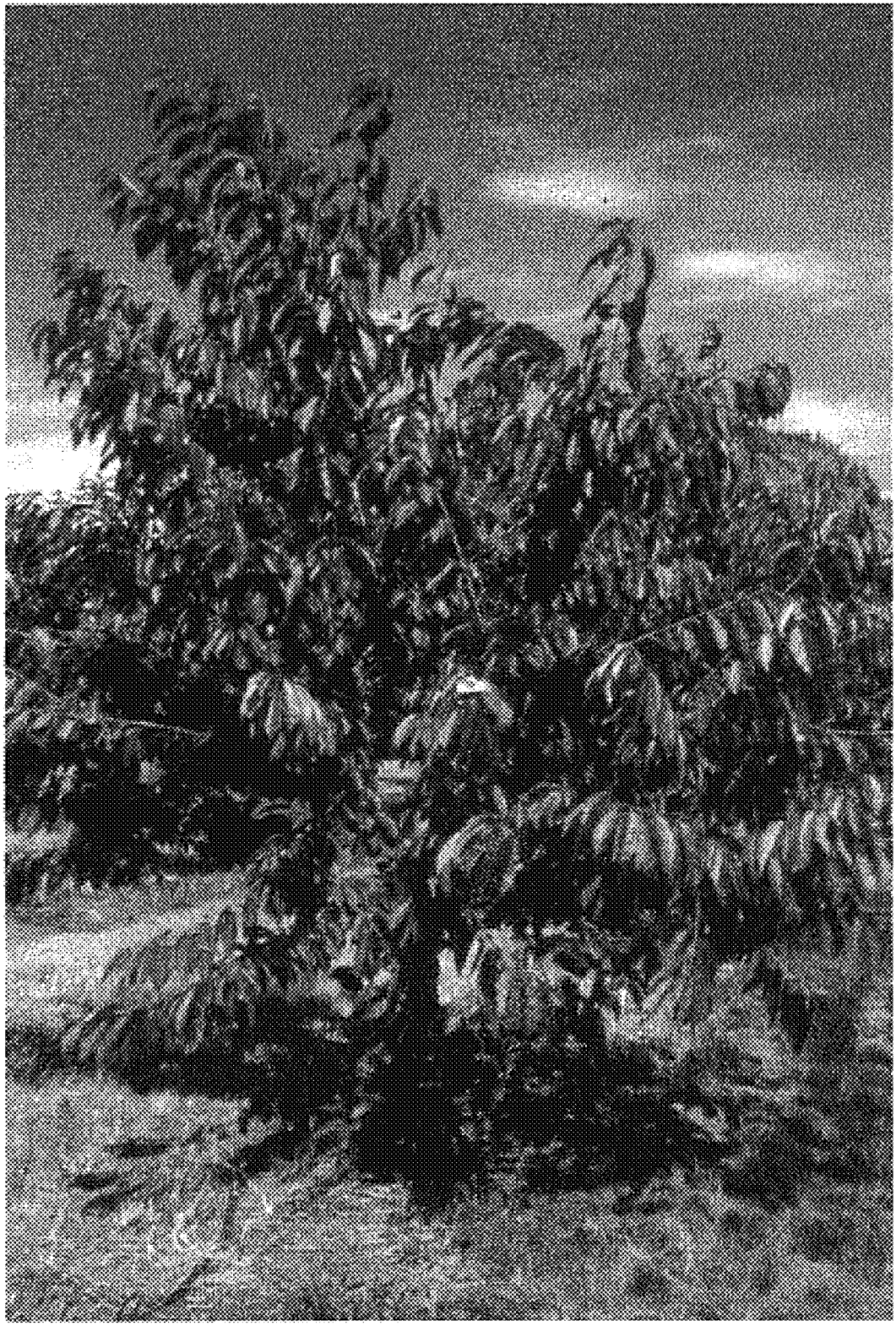

Botanical classification: *Prunus avium.*
Variety denomination: '13S2009'.

BACKGROUND OF THE INVENTION

This invention relates to cherry trees and particularly to a seedling cherry tree from an open pollination selected by Dr. W. David Lane of the Pacific Agri-Food Research Centre Summerland cherry breeding program located at Summerland, British Columbia, Canada. '13S2009' is a fruiting sweet cherry tree and has a market use as a dessert quality cherry.

The Agriculture and Agri-Food Canada research facility at Summerland was established in 1914. Originally called the Dominion Experimental Farm at Summerland, the name was changed to the Summerland Research Station in 1959, the Summerland Research Centre in 1994 and to the Pacific Agri-Food Research Centre (PARC) Summerland in 1996. The tree fruit breeding program was established in 1924 to provide new varieties for the tree fruit industry of British Columbia, Canada, and the world. The breeding program at Summerland has produced several tree fruit varieties including 'Spartan' (unpatented), 'Silken' (U.S. Plant Pat. No. 10,740), and 'Creston' (U.S. Plant Pat. No. 10,739) apples and 'Van' (unpatented), 'Lapins' (unpatented), and 'Sweetheart' (unpatented) sweet cherries. The tree fruit breeders typically produce several thousand seedlings each year.

The three broad objectives of the cherry breeding program are: 1) to diversify the product to allow growers to take advantage of niche markets; 2) to improve environmental adaptation to major fruit growing areas, for consistent production of high quality fruit; 3) to reduce the cost of production. The varieties are evaluated for the following traits to insure that the objectives are met. Primary traits include: early onset of bearing, self-compatibility, extended ripening season, fruit size, fruit firmness, and resistance to rain-induced cracking. Secondary traits include: disease resistance, winter hardiness, resistance to spring frosts, and compact tree growth habit.

Upon fruiting, the seedlings are evaluated for fruit and tree quality. Time of bloom, harvest indices, disease susceptibility and growth habit are evaluated in the field. Promising seedlings are re-propagated by budding or grafting onto rootstocks, and planted out as second test selections in variety evaluation plots. The reproductions are evaluated for varietal stability, disease susceptibility, and fruit and tree quality. The new varieties are compared to reference varieties to establish uniqueness.

The present invention relates to a new and distinct variety of cherry tree which was named '13S2009' in 2000. The original seedling was produced in 1982 and is the offspring of the seed parent 'Sweetheart' and an unknown pollen parent. The variety was planted out as a seedling in 1984 and given the Breeders Reference Number '13S-20-09' in 1991 and named "13S2009" in 2000.

History of the Invention

The present invention relates to a new and distinct variety of cherry tree which was named '13S2009' in 2000. The original cross happened in 1982 and was discovered by Dr. W. David Lane the same year. Seeds from the variety 'Sweetheart' were gathered at fruit maturity, isolated from seeds from other crosses. The seeds were subjected to the required moist chilling treatment (stratification) to enable the seeds to break dormancy in the fall of 1983. After the required stratification the seeds were germinated in a greenhouse. The resulting seedlings were transplanted into pots and grown in a greenhouse in the spring of 1984. The seedlings were taken from the greenhouse in May 1984 and planted in the seedling orchards at the PARC Summerland. A particular seedling was planted at tree position 9 in row 20 in a field designated 13 South. The seedling subsequently fruited and observations determined the fruit had unique qualities of possible commercial potential. The seedling was given the Breeders Reference Number 13S-20-09 in 1991. Four trees were created by T-budding vegetative buds of 13S-20-09 onto *P. avium* ('Mazzard' (unpatented)) rootstock in August of 1990. 'Mazzard' is the cherry rootstock of choice of most growers and nurseries in British Columbia. The stock creates full-sized trees but induces earlier fruiting with most cultivars. The resulting trees were grown in a nursery, then dug up in the fall of 1991 and stored in cold storage over winter. In the spring of 1992 the trees were removed from cold storage and planted in a field designated 4C. The resulting trees were stable in their horticultural traits and no off-types or variants occurred during the re-propagation of the instant plant. To determine fertility of the variety, blossoms of 13S-20-09 ('13S2009') were hand pollinated with pollen collected from other blossoms of '13S2009' and/or other known self-compatible varieties. The blossoms were covered with bags to inhibit pollination by bees, fruit developed normally and it can be assumed with confidence that '13S2009' is self-compatible and pollination from other sources is not required. The hand pollination and resulting determination that the variety was self-compatible also determines that the variety carries the S4' (S4 prime) allele. Polymerase chain reaction (PCR) research has determined the variety also carries the S3 allele so the compatibility group, while self-compatible, is also S3S4'.

Controlled grower trials, under test agreements, have been established in British Columbia, selected sites in the United States, and in Europe.

Stability and Propagation

In 1991, under the direction of Lane, T-budding of vegetative buds from the original plant of 13S-20-09 on Mazzard rootstock created new trees. The asexual propagation took place in Summerland, British Columbia, Canada. The resulting trees were stable and no variations occurred. Subsequent propagations have produced trees that are also stable, true-to-type and identical to the original tree in all the horticultural traits.

Distinguishing Characteristics

Under growing conditions at the Pacific Agri-Food Research Centre (PARC) Summerland located at Summerland in the Okanagan Valley of British Columbia, Canada, the variety '13S2009' consistently has the following characteristics that distinguish it from other cherry varieties. The variety is self-compatible and the fruit matures, on average, significantly later than any other commercial cherry variety. This is the variety's most distinguishing characteristic. This very late fruit maturity extends the cherry harvest season and gives a distinct financial advantage to growers. The late season maturity can help growers avoid the oversupply of cherries on the market that can happen during the peak cherry harvest season. The oversupply drives the price of cherries down, and in turn reduces the financial return to the grower. '13S2009' produces fruit of very high quality, being large with very firm flesh and having moderately glossy, red to dark red skin. The color and glossiness of the skin are very attractive when packed in a box and the firm flesh appeals to consumers and buyers. The advantage to the grower of producing '13S2009' is the lateness of fruit maturity, the visual appeal of the fruit, tolerance to rain-induced cracking, and the self-compatibility of the tree. Self-compatibility eliminates the need for pollinizer varieties and reliance on insect pollination for fruit set. Self-compatible varieties tend to produce heavier crops than self-incompatible varieties, especially during years with pool pollination weather. Poor pollination can be the result of cold, wet and/or windy conditions during the blossom period. These types of conditions restrict the movement of insects, most notably bees, and can result in low fruit set and non-profitable crops.

The fruit of '13S2009' is flattened heart-shaped and is borne on long, moderately thick stems. The fruit at maturity has red to dark red colored skin with moderate glossiness, red flesh, and a sweet taste. The fruits are very large, have very firm flesh and are resistant to rain-induced cracking. The fruit has a low prominence of suture. The stone of '13S2009' is large in absolute size, although medium in size relative to the size of the fruit. The stone is symmetrical and the shape is intermediate in the lateral view, round elliptic in the basal view and elliptic in the frontal view. The keel is strongly developed.

The leaves of '13S2009' have weak to medium glossiness on the upper side, are broad elongate in shape and have moderately shallow, dentate serrations on the leaf margins. The leaves are oriented obliquely upwards to horizontal in relation to the shoot and have cuspidate to acuminate tips and circular shaped bases. The petioles are medium in length, have anthocyanin coloration, and average more than 2, purple/red, round shaped nectaries at the base.

'13S2009' flowers about the middle of the blossom season, similar to 'Bing'. The flowers are self-compatible. The flowers are white, large in size, single in type, and appear in clusters. The pedicels are long and moderately thick. The petals are medium in size, broad elliptic to round in shape and free to touching.

The tree of '13S2009' is of moderate vigor and hardy to Zone 6A. The tree habit is upright to spreading. The tree is precocious, and very productive, and has produced good crops annually since first fruiting. The one-year-old dormant shoots show weak anthocyanin coloration and are of medium diameter at the middle of the shoot. On the average the internodes are medium in length and average a few to a medium number of small lenticels. The buds on the one-year-old dormant shoots are large in size, conical in shape and are moderately held out in relation to the shoot. The bud support is medium in diameter.

Parent Plants

'13S2009' a seedling resulting from an open pollination of the flower of the seed parent 'Sweetheart' by an unknown pollen parent.

'Sweetheart' is a result of a controlled cross of the seed parent 'Van' and the pollen parent 'Newstar' (unpatented) made at the Pacific Agri-Food Research Centre in 1975. The seedling of 'Sweetheart' tree first fruited in 1982 and continues to produce good crops annually. 'Sweetheart' became commercially available in the spring of 1994.

Seed parent:
*Name.*—'Sweetheart'.
*Species.*—*avium* L.
*Market class.*—Sweet dessert.
*Parentage.*—'Van'×'Newstar'.
Pollen parent:
*Name.*—Unknown.
*Genus.*—*Prunus.*
*Species.*—*avium* L.
*Market class.*—Unknown.

SUMMARY OF THE INVENTION

The new and distinct variety of *Prunus avium* L. fruiting cherry tree, '13S2009', resulted from open pollination of a 'Sweetheart' blossom that happened in 1982 at the Pacific Agri-Food Research Centre in Summerland, British Columbia, Canada. The seed was stratified by conventional methods and germinated in a greenhouse, and the resulting seedling tree was established in a seedling block in 1984. The seedling tree was selected for further propagation and evaluation on the basis of fruit and tree quality and the very late timing of fruit maturity, by Dr. W David Lane and given the Breeder's Reference Number '13S-20-09' in 1991. The variety has been established in a second selection block at the Pacific Agri-Food Research Centre Summerland. Evaluations began upon fruiting.

The variety has been propagated, by budding onto rootstocks under the direction of Dr. W. David Lane. The resulting trees have proved to be stable with no variations occurring. The variety demonstrates significant differences from its parents and other fruiting cherry varieties in that the fruit of '13S2009' matures very late in the cherry harvest season, is large and very firm. The skin of '13S2009' is red to dark red in color and of moderate glossiness with a few light colored highlights (dots). The flesh is dark red. The fruit is sweet (19.7% soluble solids) with a balance of sweet/sour 1.60% SSC/mg NaOH). The fruit has low susceptibility to rain-induced cracking (20% natural rain splits). The stone is symmetrical and the shape is intermediate in the lateral view, round elliptic in the basal view and elliptic in the frontal view. The keel of the stone is strongly developed.

The tree habit is upright/spreading, and moderately vigorous. The variety was first propagated in 1991 by budding on Mazzard F12/1 rootstock was established in a second selection field at the Pacific Agri-Food Research Centre at Summerland, British Columbia, Canada in 1993. The fruit of '13S2009' matures 26 to 28 days after 'Van' and 7 to 9 days after 'Sweetheart'. '13S2009' fruit is flattened heart shaped, has a slightly flattened to very slightly hollow apex, and a non-prominent suture.

Trials and Evaluations

The Pacific Agri-Food Research Centre Summerland, located at latitude 49.6 degrees north and longitude 119.6 degrees west, and about 100 feet above Okanogan Lake at an elevation of approximately 1100 feet above sea level. The Plant Hardiness Zone is 6A. The average annual precipitation is about 28 cm (11 inches). The soil types range from sandy loam to clay. All orchards in this area require irrigation and fertilization.

Test plots established at PARC Summerland consisting of 4 trees of '13S2009' were established in 1993. The variety was compared to the reference varieties 'Van', 'Sumleta' (U.S. Plant Pat. No. 11,378), 'Lapins', 'Skeena' (U.S. Plant Pat. No. 11,392), and 'Sweetheart' of approximately the same age and planted in the same area. ('Van' was used as comparator to establish harvest timing only). Controlled grower trials, under test agreements, have been established in British Columbia, selected sites in the United States and Europe.

'13S2009' was evaluated for fruit size, fruit firmness, maturity date, fruit taste (soluble solids and titratable acids), natural rain splits, tree growth habit, fruit shape, productivity, precocity and disease resistance from 1989 until the present.

Under growing conditions at the Pacific Agri-Food Research Centre (PARC) Summerland located at Summerland in the Okanagan Valley of British Columbia, Canada, the variety '13S2009' consistently has the following characteristics. '13S2009' matures on average 26 to 28 days after 'Van' and 7 to 9 days after 'Sweetheart'. 'Van' fruit mature on average about the 8th to 10th of July in Summerland. Gibberellic acid was not applied to the crop. Gibberellic acid can delay the maturity of the fruit by up to five days.

| Days After Van | Variety Name | | | | | |
|---|---|---|---|---|---|---|
| Year | Van | Sumleta | Lapins | Skeena | Sweetheart | 13S2009 |
| 1982 | 0 | | | | 8 | |
| 1983 | 0 | | 9 | | 7 | |
| 1984 | 0 | | 4 | 11 | 11 | |
| 1985 | 0 | −3 | 12 | | 10 | |
| 1987 | 0 | 16 | 16 | 16 | 35 | |
| 1988 | 0 | 3 | 1 | | | |
| 1989 | 0 | 0 | 12 | | 14 | |
| 1990 | 0 | 7 | 4 | 7 | 15 | 29 |
| 1991 | 0 | 13 | 23 | 9 | 23 | 22 |
| 1992 | 0 | 10 | 14 | 14 | | |
| 1994 | 0 | −4 | 14 | 0 | | |
| 1995 | 0 | 7 | 8 | 21 | 21 | 30 |
| 1996 | 0 | 11 | 6 | 6 | 36 | 26 |
| 1997 | 0 | 8 | 8 | 8 | 32 | 32 |
| 1998 | 0 | | | 9 | | 29 |
| 1999 | 0 | 14 | 13 | 14 | 13 | 23 |
| 2000 | 0 | 16 | 7 | 13 | 16 | 27 |
| | | 98 | 151 | 128 | 241 | 218 |
| Average days past Van | | 8 | 10 | 11 | 19 | 27 |

'Van' is harvested about the 8th to 10th of July at Summerland

The variety has an average fruit weight of 11.4 g, similar to 'Lapins' (11.7 g) and 'Skeena' (11.5 g), significantly larger than 'Sweetheart' (10.1 g), and significantly smaller 'Sumleta' (13.1 g). 'Lapins', 'Sumleta' and 'Skeena' are considered to have large fruit, 'Sweetheart' is considered to have moderately large fruit.

| Average fruit weight | Variety Name | | | | |
|---|---|---|---|---|---|
| Year | Sumleta | Lapins | Skeena | Sweetheart | 13S2009 |
| 1991 | 12.9 | 12.4 | 12.6 | 11.0 | 12.2 |
| 1993 | 13.4 | 12.1 | 11.3 | 9.9 | 11.8 |
| 1995 | 13.7 | 11.9 | 12.1 | 10.0 | 11.3 |
| 1996 | 12.6 | 9.8 | 10.8 | 10.4 | 11.4 |
| 1997 | 12.2 | 11.1 | 9.8 | 8.1 | 11.3 |

-continued

| Average fruit weight | Variety Name | | | | |
|---|---|---|---|---|---|
| Year | Sumleta | Lapins | Skeena | Sweetheart | 13S2009 |
| 1999 | 12.8 | 12.2 | 11.5 | 11.0 | 11.2 |
| 2000 | 14.4 | 12.0 | 12.5 | 10.1 | 10.8 |
| Total | 91.9 | 81.6 | 80.6 | 70.4 | 80.0 |
| Average over 7 years | 13.1 | 11.7 | 11.5 | 10.1 | 11.4 |

The flesh is significantly firmer than 'Lapins', slightly firmer than 'Sumleta', and as firm as 'Sweetheart' and 'Skeena'. Over 5 years, '13S2009', 'Skeena', and 'Sweetheart' had a mean rating of 81 in firmness as measured by Shores Durometer, whereas 'Sumleta' averages 79 and 'Lapins' 76. 'Sweetheart' is considered to be a very firm variety by commercial growers. Gibberellic acid was not applied to any of these test samples. In commercial plantings, gibberellic acid is used to improve the firmness and delay the maturity of cherry fruit.

| Flesh Firmness | Variety name | | | | |
|---|---|---|---|---|---|
| Year | Sumleta | Lapins | Skeena | Sweetheart | 13S2009 |
| 1995 | 79 | 78 | 82 | 83 | 85 |
| 1996 | 85 | 83 | 85 | 79 | 80 |
| 1997 | 80 | 76 | 77 | 84 | 83 |
| 1999 | 76 | 72 | 80 | 79 | 76 |
| 2000 | 75 | 72 | 81 | 79 | 80 |
| Total | 395 | 381 | 405 | 404 | 404 |
| 5 year Average | 79 | 76 | 81 | 81 | 81 |

The fruit of '13S2009' on average has a high soluble solids concentration (SSC) similar to 'Sumleta', 'Skeena', and 'Sweetheart' and significantly higher than 'Lapins'. '13S2009' has a moderate amount of titratable acid (TA), similar to 'Skeena' and 'Sweetheart', significantly more than 'Lapins' and significantly less than 'Sumleta'. The balance between SSC and TA in '13S2009' gives the fruit a sweet taste. The SSC/TA balance does reflect the sensory perception of sweetness in the fruit. For example 'Sumleta' has a lower ratio than the others, reflecting a more acidic taste. This is consistent with human perception of the taste even though 'Sumleta' has higher soluble solids than most other dark or red cherries.

| | Variety Name | | | | |
|---|---|---|---|---|---|
| Year | Sumleta | Lapins | Skeena | Sweetheart | 13S2009 |
| Soluble Solids | | | | | |
| 1995 | 22.7 | 20.9 | 17.8 | 20.7 | 21.3 |
| 1996 | 17.9 | 17.9 | 17.3 | 19.1 | 19.6 |
| 1997 | 20.2 | 21.9 | 16.6 | 19.4 | 18.9 |
| 1999 | 21 | 21 | 19.6 | 21.9 | 20.3 |
| 2000 | 19.3 | 17.6 | 15.5 | 18.9 | 18.5 |
| Total | 101.1 | 99.3 | 86.8 | 100 | 98.6 |
| Average | 20.22 | 19.86 | 17.36 | 20 | 19.72 |

-continued

| | Variety Name | | | | |
|---|---|---|---|---|---|
| Year | Sumleta | Lapins | Skeena | Sweetheart | 13S2009 |
| Titratable Acidity | | | | | |
| 1995 | 14.17 | 13.52 | 8.39 | 12.73 | 12.06 |
| 1996 | 15.93 | 13.94 | 12.25 | 12.13 | 11.41 |
| 1997 | 12.41 | 12.58 | 8.34 | 10.77 | 9.72 |
| 1999 | 16.4 | 14.8 | 11.3 | 15.4 | 14.5 |
| 2000 | 15.75 | 14.15 | 10.95 | 13.1 | 14.25 |
| Total | 74.66 | 68.99 | 51.23 | 64.13 | 61.94 |
| Average | 14.932 | 13.798 | 10.246 | 12.826 | 12.388 |
| SSC/TA Balance | | | | | |
| 1995 | 1.60 | 1.55 | 2.12 | 1.63 | 1.77 |
| 1996 | 1.12 | 1.28 | 1.41 | 1.57 | 1.72 |
| 1997 | 1.63 | 1.74 | 1.99 | 1.80 | 1.94 |
| 1999 | 1.28 | 1.42 | 1.73 | 1.42 | 1.40 |
| 2000 | 1.23 | 1.24 | 1.42 | 1.44 | 1.30 |
| Total | 1.35 | 1.44 | 1.69 | 1.56 | 1.59 |
| SSC/Total TA | | | | | |

'13S2009' has a significantly lower tendency to crack due to rain than most other varieties. 'Lapins' is considered to be highly tolerant of rain-induced cracking. Rain-induced cracking is difficult to reproduce annually, as it is dependent on the weather during the latter part of the fruit maturation period. 'Sweetheart' for example is very susceptible to rain-induced cracking, but over a 7 year period it appears to have about the same resistance as 'Lapins'. However from observation and grower comments it has been established that '13S2009', 'Lapins', and 'Skeena' are much less prone to rain-induced cracking than are 'Sweetheart' and 'Sumleta'. This could be a reflection of the area where the cherries are grown. The Okanagan Valley of British Columbia receives a total yearly average of about 28 cm (11 inches) of precipitation, with June typically receiving the most rain during the summer months. As the late season cherries do not mature until late July or after, they are past the heavy rain periods and are subject only to short storm periods after turning from straw color to red. Cherries split more after turning red. The same observations and comments indicate '13S2009' is more tolerant to cracking than 'Lapins' and 'Skeen'.

| % Rain induced Cracking | Variety Name | | | | |
|---|---|---|---|---|---|
| Year | Sumleta | Lapins | Skeena | Sweetheart | 13S2009 |
| 1991 | 35 | 21 | 23 | 20 | 15 |
| 1993 | 55 | 44 | 18 | 30 | 9 |
| 1995 | 34 | 7 | 25 | 26 | 14 |
| 1996 | 33 | 26 | 28 | 49 | 27 |
| 1997 | 61 | 38 | 32 | 48 | 32 |
| 1999 | 23 | 25 | 22 | 7 | 26 |
| 2000 | 51 | 22 | 15 | 24 | 16 |
| Average % R.I.C. | 291 | 183 | 163 | 204 | 139 |
| Total Average | 42 | 26 | 23 | 29 | 20 |

The tree of '13S2009' is upright to somewhat spreading and has moderate vigor similar to 'Sweetheart' and unlike 'Lapins' which is very upright and very vigorous. The tree of '13S2009' requires much less effort to produce a well-balanced tree than most commercial cultivars. The one-year-shoots are moderately horizontal in relation to the tree, similar to 'Sweetheart'. This branching habit is conducive to flower bud initiation and high fruit set and yield. The tree produces lateral branches readily after heading at planting. Dormant pruning is required to remove upright shoots for improved penetration of sunlight and pesticide sprays, and to renew fruiting wood. Other manipulations, such as hormone application or scoring, to encourage branching are unnecessary. Higher quality cherries are produced on $2^{nd}$ and $3^{rd}$ year wood, therefore branch renewal is vital. '13S2009' produces very heavy crops annually and may require thinning by hand of blossoms or fruit, or by pruning off parts off fruiting areas of limbs to reduce the crop load and maintain large fruit size.

'13S2009' has been propagated by budding onto Colt (U.S. Plant Pat. No. 4,059 expired), Mazzard (unpatented), Mazzard F12/1 (unpatented), Mahaleb (unpatented), and Gisela 5 (U.S. Plant Pat. No. 9,622) rootstocks with no unusual or unique occurrences that set it apart from other varieties. It is graft compatible with all these rootstocks provided that virus-certified propagation wood is used.

Virus Status and Disease Susceptibility/Resistance

Wood of '13S2009' has been virus indexed at the Centre for Plant Health at Sidney B.C., Canada. Virus-certified trees have been made and established and are being maintained at the okanagan Plant Improvement Company's certified bud wood orchard at Summerland, B.C., Canada.

'13S2009' has shown neither unusual susceptibility nor resistance to any plant or fruit pests and/or diseases compared to other cultivars.

BRIEF DESCRIPTIONS OF THE DRAWINGS

The accompanying photographs show various characteristics of the cherry variety '13S2009'. The colors of the photographs are as nearly true as is possible in a color representation of this type.

In FIG. 1, a typical tree is shown. The photograph shows the growth habit a typical tree, approximately 7 years years old, slightly before optimum maturity of the fruit.

Figure 2:
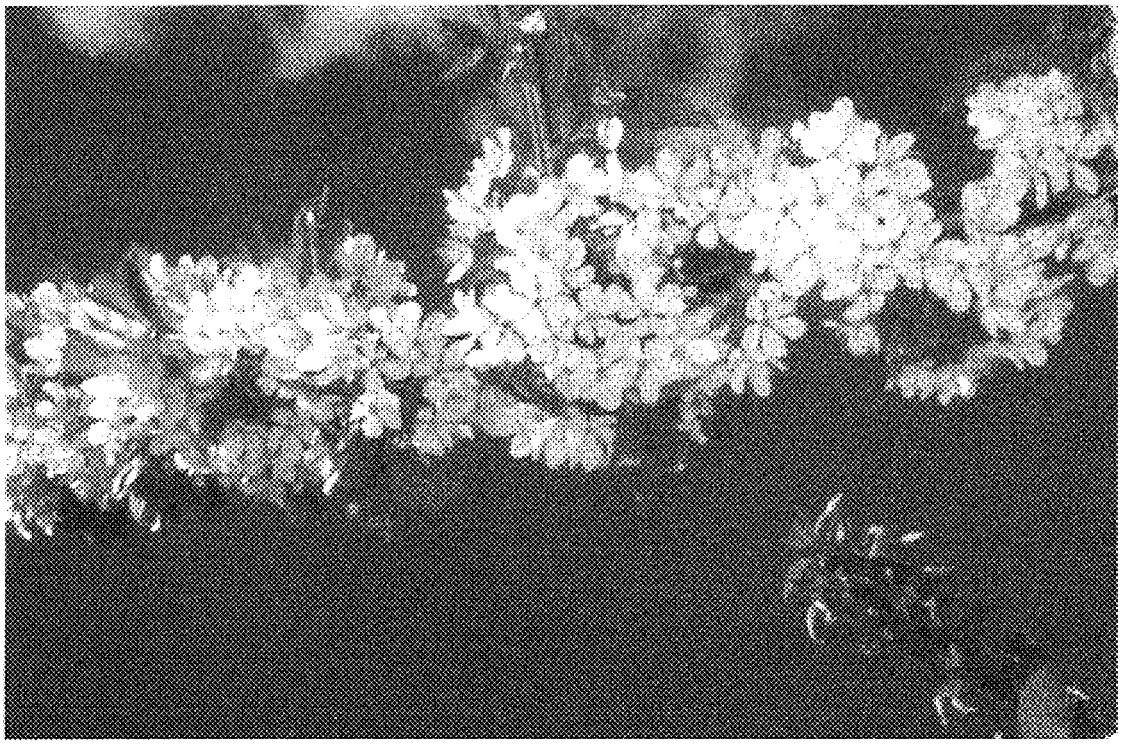

In FIG. 2, a typical branch at blossom is shown. The photograph displays the blossoms of '13S2009' at about full bloom.

Figure 3:
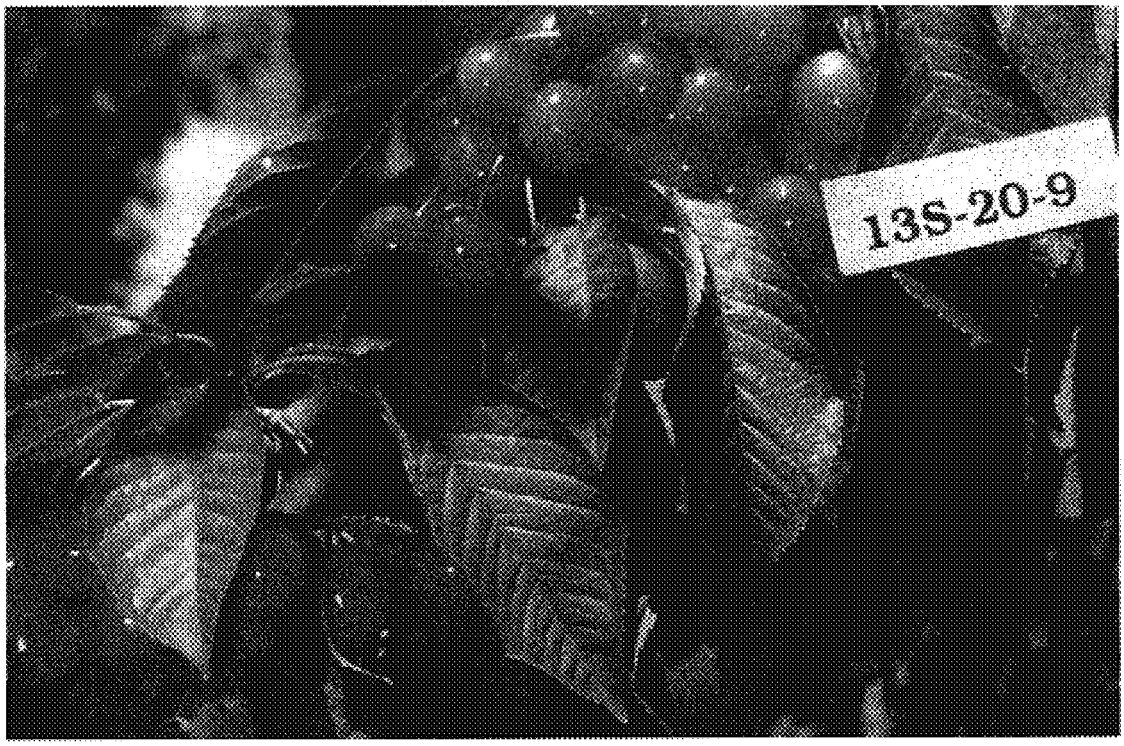

FIG. 3 shows a typical branch with fruit somewhat prior to harvest. The photograph illustrates the cluster of fruit and the leaves of the variety.

Figure 4:
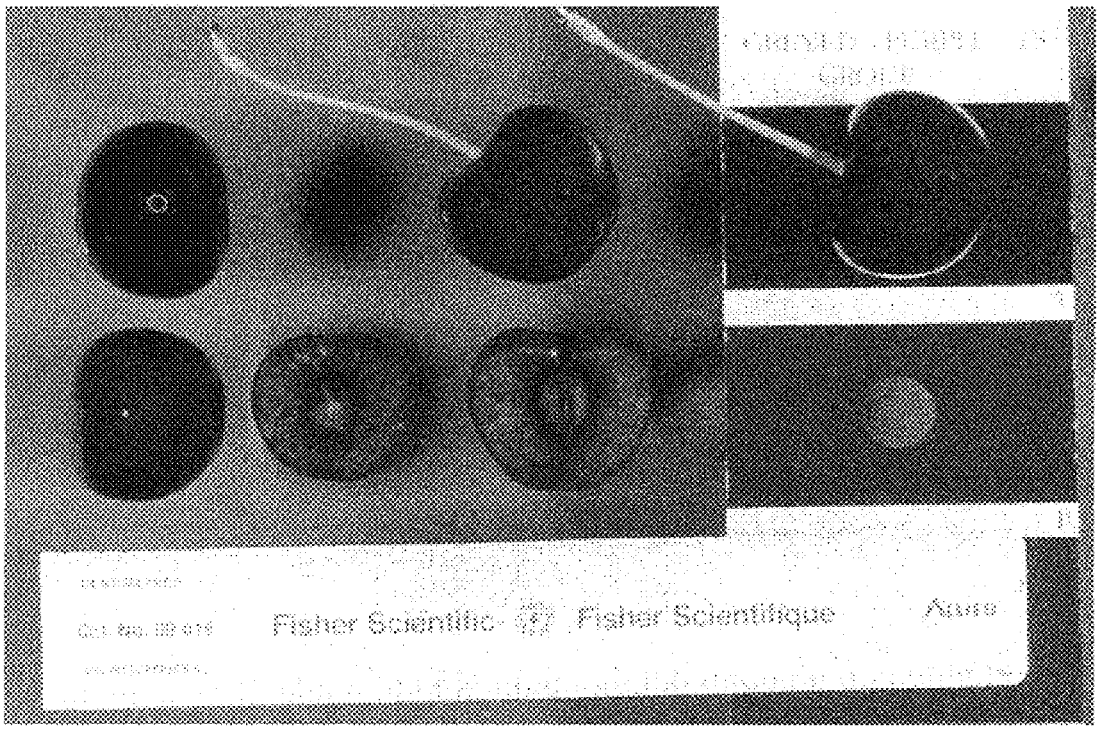

FIG. 4 comprises view of the mature fruit of '13S2009' in large scale. The fruit is arranged to display the blossom end (top) and the side view (middle left) of the fruit. These views show the color of the fruit at maturity in the middle right the fruit is displayed in cross section after being cut centrally across the midline. The flesh color and the arrangement of the flesh in relation to the stone is displayed.

Figure 5:
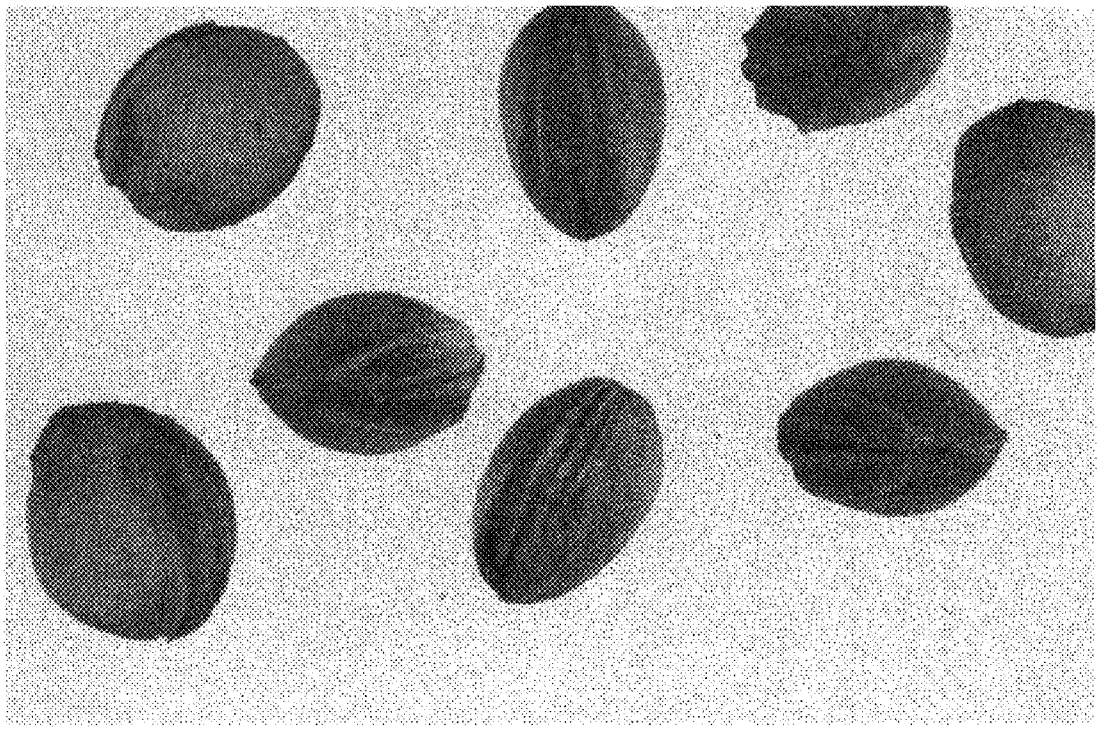

In FIG. 5, various views of the stone are displayed of the fruit, after drying and the flesh is removed. The basal, lateral and front views are displayed as well as views of the keel.

DETAILED BOTANICAL DESCRIPTION

The following is a detailed description of '13S2009'. All trees are of approximately the same age and have Mazzard F12/1 for rootstock. The color determination is in accordance with the R.H.S. Colour Chart of The Royal Horticultural Society, London, England, except where general color terms of ordinary dictionary significance are used.

Fruit end use: Dessert.

Group: Sweet dark.

Growth characteristics: (Observations are measurements from 6-year-old bearing trees).

- *Tree vigor.*—Moderate.
- *Tree height.*—5 meters.
- *Tree width.*—4 meters.
- *Growth habit.*—Upright to spreading.
- *Branch pubescence.*—Absent or very weak.
- *Bearing.*—Annual and regular.

Shoot characteristics: (Observations from 10 one-year-old dormant shoots).

- *Shoot attitude.*—Slightly horizontal.
- *Vegetative bud size.*—Large. Mean: 7.06 mm. Range: 1.56 mm.
- *Bud support width.*—Medium. Mean: 3.57 mm. Range: 1.17 mm.
- *Wood bud shape.*—Conical.
- *Position of bud.*—Moderately held out from the shoot.
- *Number of lenticels.*—Medium (71 per 12 cm from middle of the shoot).
- *Shoot diameter (middle of internode).*—Mean: 6.14 mm. Range: 1.43 mm.
- *Internode length (middle of shoot).*—Mean: 35.02 mm. Range: 32.85 mm.
- *Anthocyanin coloration (shoot tip).*—Weak.
- *Bark coloration 1st year wood.*—165A (RHS) (at dormant).
- *Bark coloration mature branch.*—177A (RHS) (at dormant).
- *Bark coloration trunk.*—177A (RHS) (at dormant).

Leaf characteristics: (Measurements are the mean of 10 leaves).

- *Bud burst in relation to full flowering.*—Much earlier.
- *Attitude to shoot.*—Horizontal to slightly obliquely upwards.
- *Leaf shape.*—Broad elongate.
- *Angle at blade tip.*—Acute to almost right angle.
- *Shape of base.*—Rounded.
- *Shape of apex.*—Cuspidate to acuminate.
- *Leaf blade profile shape.*—Slightly concave.
- *Leaf color (adaxial).*—Medium green 137A (RHS).
- *Leaf color (abaxial).*—137C (RHS).
- *Anthocyanin upper side.*—Absent.
- *Anthocyanin (leaf glands).*—187B (RHS).
- *Glossiness.*—Weak to medium.
- *Margin indentation.*—Dentate.
- *Degree of indentation.*—Shallow.
- *Leaf blade length.*—Mean: 176.33 mm. Range: 51.0 mm.
- *Leaf blade width.*—Mean: 79.8 mm. Range: 22 mm.
- *Blade ratio.*—Length/width: 2.11.
- *Petiole length.*—Mean: 39.87 mm. Range: 15 mm.
- *Petiole to leaf blade ratio (length).*—4.47.
- *Petiole anthocyanin.*—71A (RHS).
- *Number of nectaries (out of 10).*—More than 2.
- *Nectaries color.*—Purple red 60A (RHS).
- *Nectaries shape.*—Round to reniform.
- *Nectaries position.*—Predominately occur alternately positioned located on the stem, rarely positioned oppositely.

Flower characteristics: (Measurements are the mean of 10 flowers).

*Bloom period.*—Middle of bloom season.
*Flower appearance.*—In clusters.
*Flowers per cluster.*—10 to 12.
*Duration of bloom.*—7 to 10 days.
*Flowering density.*—Medium.
*Flower type.*—Single, perfect, complete, perigynous.
*Flower color.*—White.
*Flower size* (*diameter of corolla*).—Mean: 41.5 mm. Range: 7.0 mm.
*Pedicel length.*—Mean: 33.3 mm. Range: 17.0 mm.
*Pedicel thickness.*—Mean: 1.09 mm. Range: 0.11 mm.
*Pedicel pubescence.*—Absent or very weak.
*Petal size* (*length*).—Mean: 18.50 mm. Range: 2.0 mm.
*Petal size* (*width*).—Mean: 15.80 mm. Range: 2.00 mm.
*Petal shape.*—Broad elliptic to slightly round.
*Petal position of margins.*—Touching.
*Petal color.*—White 155D (RHS).
*Anther color* (*at dehiscence*).—Yellow/green 153B (RHS).
*Frequency of supplementary pistil.*—Absent.
*Pistil presence.*—Normal Pistil.
*Ovary pubescence.*—Absent.

Fruit characteristics: (Measurements are the means from a 10-fruit sample).

*Maturity date.*—Very Late (average 1st week August at Summerland, 27 days after 'Van' at Summerland).
*Weight* (*average*).—11.4 g (50 fruit sample).
*Large diameter.*—Mean: 29.50 mm. Range: 3.30 mm.
*Fruit length.*—Mean: 25.7 mm. Range: 2.97 mm.
*Shape.*—Flattened Heart.
*Profile in lateral view.*—Flattened.
*Symmetry of fruit.*—Symetrical.
*Position of largest diameter.*—Towards the middle.
*Suture.*—Low.
*Fruit apex.*—Flat to very slightly hollow.
*Color of flesh.*—Dark red 187B (RHS).
*Color of skin.*—Wine Red 187A (RHS).
*Dots on skin.*—Few (medium in size).
*Glossiness.*—Average.
*Firmness of flesh.*—Very firm (81 by Shores Durometer).
*Rain induced cracking.*—Low (20%).
*Fruit taste.*—Sweet.
*Soluble sold concentration.*—19.7% (over 5 years).
*Titratable acids* (*mg NaOH*).—12.4 (over 5 years).
*SSC/TA balance.*—1.59 (over 5 years).
*Juice color.*—Dark red 187A (RHS).
*Fruit juiciness.*—Medium.
*Length of stalk.*—Mean: 52.13 mm. Range: 16.0 mm.
*Stalk thickness.*—Mean: 1.01 mm. Range: 0.43 mm.
*Adherence of flesh to stone.*—Slightly adherent.
*Stone color.*—159A (RHS).
*Stone size* (*length*).—Large. Mean: 11.5 mm. Range: 1.97 mm.
*Stone size* (*dia.*).—Mean: 10.47 mm. Range: 2.09 mm.
*Stone size relative to fruit.*—Medium.
*Shape in lateral view.*—Intermediate.
*Stone shape front view.*—Elliptic.
*Stone shape in basal view.*—Round elliptic.
*Stone symmetry in lateral view.*—Symmetrical.
*Stone keel development.*—Strongly developed.
*Compatibility.*—Self-compatible.
*Precocity of bearing.*—Intermediate to high.
*Fruit set* (*yield efficiency*).—Very high.
*Storage.*—2 weeks at 0C (slightly less than 'Bing').
*Storage.*—4 weeks in Modified Atmosphere packing (MAP).

It is claimed:

1. A new and distinct variety of sweet cherry tree named '13S2009' substantially as herein illustrated and described.

* * * * *